(12) United States Patent
Patel et al.

(10) Patent No.: US 9,797,784 B2
(45) Date of Patent: Oct. 24, 2017

(54) COMMUNICATION AND MONITORING OF A BATTERY VIA A SINGLE WIRE

(71) Applicant: Apple Inc., Cupertino, CA (US)

(72) Inventors: Parin Patel, San Francisco, CA (US); Scott P. Mullins, Morgan Hill, CA (US)

(73) Assignee: Apple Inc., Cupertino, CA (US)

( * ) Notice: Subject to any disclaimer, the term of this patent is extended or adjusted under 35 U.S.C. 154(b) by 525 days.

(21) Appl. No.: 13/726,503

(22) Filed: Dec. 24, 2012

(65) Prior Publication Data

US 2013/0235902 A1    Sep. 12, 2013
US 2016/0223412 A9    Aug. 4, 2016

Related U.S. Application Data

(60) Provisional application No. 61/607,911, filed on Mar. 7, 2012.

(51) Int. Cl.
*G01K 1/12* (2006.01)
*G01K 1/14* (2006.01)
(Continued)

(52) U.S. Cl.
CPC .............. *G01K 13/00* (2013.01); *A61K 31/56* (2013.01); *G01N 33/5041* (2013.01);
(Continued)

(58) Field of Classification Search
CPC ...... H02J 7/0022; H02J 7/0081; H02J 7/0086; H02J 7/1446; H02J 7/0021;
(Continued)

(56) References Cited

U.S. PATENT DOCUMENTS 3,534,241 A * 10/1970 Trenkler et al. .............. 320/144
5,371,453 A   12/1994 Fernandez
(Continued)

FOREIGN PATENT DOCUMENTS

CN       1182482 A    5/1998
CN     101295881 A   10/2008
(Continued)

*Primary Examiner* — Gail Kaplan Verbitsky
(74) *Attorney, Agent, or Firm* — Blank Rome LLP

(57) ABSTRACT

A power-management unit is described. This power-management unit allows a common signal line to communicate data between an integrated circuit (which may be external to the power-management unit) and a battery-monitoring mechanism in a battery pack, and to convey a signal that represents a temperature state of the battery pack to a temperature-monitoring circuit or mechanism that monitors the temperature state of the battery pack. In particular, the power-management unit may include a single-wire interface or a multiplexer that, at a given time, selectively couples the signal line from the battery pack either to the integrated circuit or the temperature-monitoring circuit based on a control signal provided by the integrated circuit (for example, via an I2C bus or interface). In this way, the power-management unit may reduce the number of signal lines needed to communicate with the battery-monitoring mechanism and to convey the signal.

19 Claims, 6 Drawing Sheets

(51) Int. Cl.

| | | |
|---|---|---|
| *G01K 13/00* | (2006.01) | |
| *G06F 1/20* | (2006.01) | |
| *G06F 1/32* | (2006.01) | |
| *H01M 10/42* | (2006.01) | |
| *H01M 10/48* | (2006.01) | |
| *A61K 31/56* | (2006.01) | |
| *G01N 33/50* | (2006.01) | |
| *H01M 10/44* | (2006.01) | |

(52) U.S. Cl.
CPC ............. *G06F 1/206* (2013.01); *G06F 1/32* (2013.01); *G06F 1/3206* (2013.01); *H01M 10/425* (2013.01); *H01M 10/443* (2013.01); *H01M 10/486* (2013.01); *G01N 2500/00* (2013.01); *H01M 2010/4271* (2013.01); *H01M 2010/4278* (2013.01); *Y02B 60/1275* (2013.01)

(58) Field of Classification Search
CPC ............ H02J 2007/0037; H02J 7/0008; H02J 7/0019; H02J 7/0026; H02J 7/047; H02J 7/008; H01M 10/486; H01M 10/443; H01M 10/482; H01M 2200/10; H01M 10/441; H01M 10/4207; B60K 35/00
USPC ........ 374/170, 141, 153, 183, 163, 185, 152; 320/154
See application file for complete search history.

(56) References Cited

U.S. PATENT DOCUMENTS

| | | | |
|---|---|---|---|
| 5,414,860 A | 5/1995 | Canova | |
| 5,504,416 A * | 4/1996 | Holloway et al. | 320/152 |
| 5,886,527 A | 3/1999 | Ito | |
| 5,912,548 A | 6/1999 | Downs | |
| 6,005,367 A | 12/1999 | Rohde | |
| 6,107,780 A * | 8/2000 | Kellerman | 320/132 |
| 6,549,014 B1 * | 4/2003 | Kutkut et al. | 324/426 |
| 6,771,042 B2 * | 8/2004 | Chen et al. | 320/110 |
| 7,317,298 B1 | 1/2008 | Burns | |
| 8,217,628 B2 * | 7/2012 | Yang et al. | 320/134 |
| 8,319,479 B2 * | 11/2012 | Kao et al. | 320/157 |
| 8,808,886 B2 * | 8/2014 | Kim | 429/61 |
| 8,957,639 B2 * | 2/2015 | Holsen et al. | 320/134 |
| 8,961,004 B2 * | 2/2015 | Srinivasan | H01M 2/34 320/150 |
| 2003/0117112 A1 | 6/2003 | Chen | |
| 2004/0169489 A1 | 9/2004 | Hobbs | |
| 2005/0099156 A1 | 5/2005 | Brenner | |
| 2005/0194935 A1 | 9/2005 | Kubota | |
| 2006/0139007 A1 | 6/2006 | Kim | |
| 2006/0226814 A1 | 10/2006 | Formenti | |
| 2007/0090788 A1 | 4/2007 | Hansford | |
| 2007/0257642 A1 | 11/2007 | Xiao | |
| 2008/0018300 A1 * | 1/2008 | Zaag | H02J 7/0019 320/118 |
| 2008/0120513 A1 | 5/2008 | Kim | |
| 2009/0039836 A1 | 2/2009 | Asada | |
| 2009/0174370 A1 | 7/2009 | Gilling | |
| 2009/0230923 A1 * | 9/2009 | Hoffman et al. | 320/136 |
| 2009/0295334 A1 * | 12/2009 | Yang et al. | 320/134 |
| 2010/0085018 A1 | 4/2010 | Cruise | |
| 2010/0270973 A1 * | 10/2010 | Miyazaki et al. | 320/120 |
| 2012/0286732 A1 * | 11/2012 | Cruise et al. | 320/112 |
| 2013/0038293 A1 * | 2/2013 | Seman, Jr. | H02J 7/0019 320/134 |
| 2013/0082662 A1 * | 4/2013 | Carr et al. | 320/134 |
| 2016/0118840 A1 * | 4/2016 | Shinoda | H01M 10/46 320/108 |
| 2017/0141592 A1 * | 5/2017 | Snyder | H02J 7/0031 |

FOREIGN PATENT DOCUMENTS

| | | | |
|---|---|---|---|
| CN | 101529646 A | | 9/2009 |
| CN | 101741403 A | | 6/2010 |
| EP | 0661769 A2 | | 7/1995 |
| EP | 0936719 A2 | | 8/1999 |
| EP | 1291999 A1 | | 3/2003 |
| EP | 2290781 A2 | | 3/2011 |
| EP | 2293781 A2 | | 3/2011 |
| JP | 2004311240 A | * | 11/2004 |
| JP | 2005131770 A | | 5/2005 |

* cited by examiner

COMMUNICATION AND MONITORING OF A BATTERY VIA A SINGLE WIRE

CROSS REFERENCE TO RELATED APPLICATIONS

This application claims priority under 35 U.S.C. §119(e) to U.S. Provisional Application Ser. No. 61/607,911, entitled "Communication and Monitoring of a Battery Via a Single Wire," by Parin Patel and Scott P. Mullins, filed on Mar. 7, 2012, the contents of which is herein incorporated by reference.

This application is also related to: U.S. Patent Application Ser. No. 61/607,916, entitled "Charging a Battery Based on Stored Battery Characteristics," by Parin Patel and Scott P. Mullins, filed Mar. 7, 2012, the contents of which are herein incorporated by reference.

BACKGROUND

Field

The described embodiments relate to techniques for monitoring and communicating with a battery pack. More specifically, the described embodiments relate to techniques for communicating data and a signal representing a temperature state of the battery pack via a common signal line.

Related Art

The ever-increasing functionality and performance of portable electronic devices is, in part, due to advances in power sources, such as battery packs. Modern battery packs in portable electronic devices typically include circuits that monitor characteristics of the battery packs, for example, the voltage across a battery in a battery pack, a charging current, an internal impedance, the available capacity, etc. This information is typically communicated to a host portable electronic device via one or more signal lines.

In addition, for safety reasons, it is often important to at least periodically monitor the temperature of a battery pack. For example, the temperature of the battery pack may be monitored during charging. The temperature of the battery pack is typically conveyed to a host portable electronic device via a separate signal line from the one used to convey the other characteristics of the battery pack.

However, having separate signal lines to convey the battery pack characteristics and the temperature consumes valuable area or real estate in portable electronic devices, thereby increasing the cost. In addition, these separate signal lines increase the complexity and the power consumption in portable electronic devices.

SUMMARY

The described embodiments include a power-management unit that allows a common signal line to communicate data between an integrated circuit (which may be external to the power-management unit) and a battery-monitoring mechanism in a battery pack, and to convey a signal that represents a temperature state of the battery pack to a temperature-monitoring circuit or mechanism that monitors the temperature state of the battery pack. In particular, the power-management unit may include a single-wire interface or a multiplexer that, at a given time, selectively couples the signal line from the battery pack either to the integrated circuit or to the temperature-monitoring circuit based on a control signal (such as a timing signal) provided by the integrated circuit (for example, via an I2C bus or interface). In this way, the power-management unit may reduce the number of signal lines needed to communicate with the battery-monitoring mechanism and to convey the signal.

The temperature state may indicate whether it is safe to charge the battery pack. Therefore, the power-management unit may selectively couple the battery pack and the temperature-monitoring circuit when the battery pack is coupled to a charger. Furthermore, for safety reasons the selective coupling to the temperature-monitoring circuit may be periodic. In addition, this coupling may be a default configuration or condition of the multiplexer, and the power-management unit may revert to this default condition a time interval after the multiplexer selectively couples the battery pack and the integrated circuit. In this way, the temperature state of the battery pack can be monitored even if the control signal is not provided by the integrated circuit.

In some embodiments where a host (e.g., the integrated circuit) is in a power-saving mode (such as a 'sleep' mode), the signal line can be used to convey a wake signal from the battery-monitoring mechanism to transition the host to a normal operating mode. Because this wake signal can be conveyed when either the integrated circuit or the temperature-monitoring circuit is selectively coupled to the battery pack, the wake signal may be detected by a wake circuit in the power-management unit and/or by the temperature-monitoring circuit.

In some embodiments, when the multiplexer selectively couples the signal line to the integrated circuit, the signal line is also coupled to a supply voltage via a pull-up resistor so that the signal line is pulled to the supply voltage.

Another embodiment provides an electronic device that includes the battery pack, the integrated circuit and the power-management unit, which is coupled to the battery pack by the signal line. This battery pack may include: a battery; the battery-monitoring mechanism that monitors characteristics of the battery; a temperature sensor; and the signal line, which is electrically coupled to the battery-monitoring mechanism and the temperature sensor.

Another embodiment provides a method for conveying the signal that represents the temperature state of the battery pack and communicating data between the integrated circuit and the battery pack on the signal line, which may be performed by the power-management unit. Based on the control signal, the power-management unit selectively couples the signal line to the integrated circuit that communicates with the battery-monitoring mechanism in the battery pack. Subsequently, based on the control signal, the power-management unit selectively couples the signal line to the temperature-monitoring circuit that determines the temperature state of the battery pack.

BRIEF DESCRIPTION OF THE FIGURES

Note that like reference numerals refer to corresponding parts throughout the drawings. Moreover, multiple instances of the same part are designated by a common prefix separated from an instance number by a dash.

DETAILED DESCRIPTION

Figure 1:
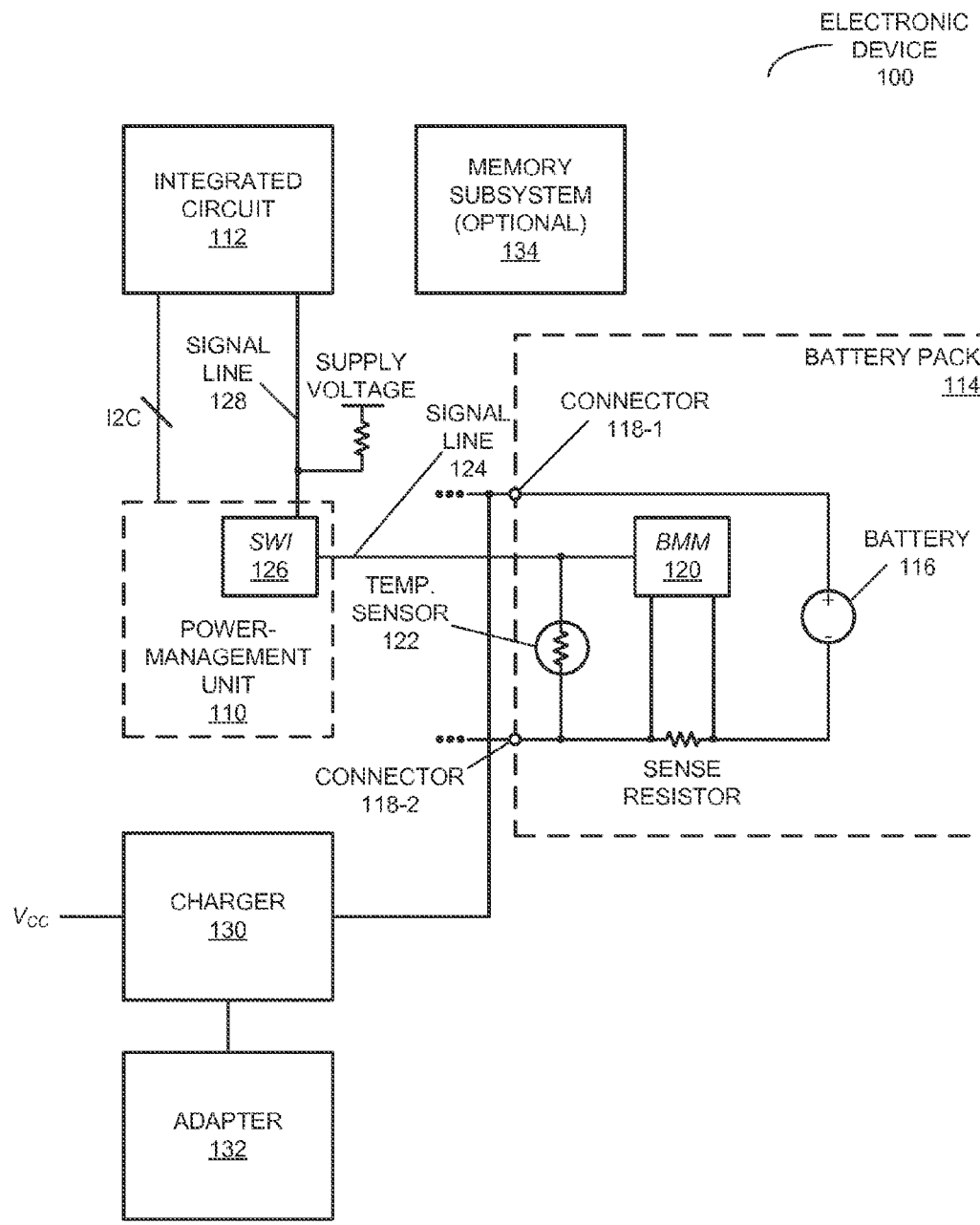
FIG. 1 presents a block diagram illustrating an electronic device that includes a power-management unit, an integrated circuit and a battery pack in accordance with an embodiment of the present disclosure.

FIG. 1 presents a block diagram illustrating an electronic device 100 that includes a power-management unit 110, an integrated circuit 112 (such as a processor, a graphics processor and/or a system-on-chip) and a battery pack 114. Battery pack 114 may include: a battery 116 that provides power to electronic device 100 via connectors 118; a battery-monitoring mechanism or BMM 120 (such as control logic and/or firmware, which is sometimes collectively referred to as a 'gas gauge') that monitors one or more physical characteristics of battery pack 114 and/or battery 116 (such as a voltage, a current, an internal impedance, a capacity, a charging time, etc.); a temperature sensor 122 (such as a thermistor) that measures a temperature of battery pack 114 and/or battery 116; and a signal line 124, which electrically couples battery-monitoring mechanism 120 and temperature sensor 122 to power-management unit 110.

Note that battery pack 114 is electrically coupled to a remainder of electronic device 100 by three signal lines (instead of four), including those associated with power and ground connectors 118 (which are not shown for clarity) and signal line 124 (which, as described below, combines temperature monitoring and data communication). As a consequence, an area in electronic device 100 needed to interface with battery pack 114 is reduced, thereby reducing the cost and complexity of battery pack 114 and electronic device 100.

This reduction in the number of signal lines is facilitated by alternating use of signal line 124 to communicate data between battery-monitoring mechanism 120 and integrated circuit 112, and to convey a signal from temperature sensor 122 that represents a temperature (and, more generally, a temperature state) of battery pack 114 and/or battery 116. This sharing of signal line 124 is facilitated by power-management unit 110. In particular, power management unit 110 may include a single-wire interface (SWI) 126. In the discussion that follows, single-wire interface 126 is illustrated by a multiplexer, and integrated circuit 112 implements a single-wire communication protocol, such as HDQ serial data interface (from Texas Instruments, Inc. of Dallas, Tex.), on signal line 128 for use in communicating data with battery-monitoring mechanism 120. (However, in other embodiments single-wire interface 126 implements the single-wire communication protocol.)

Figure 2:
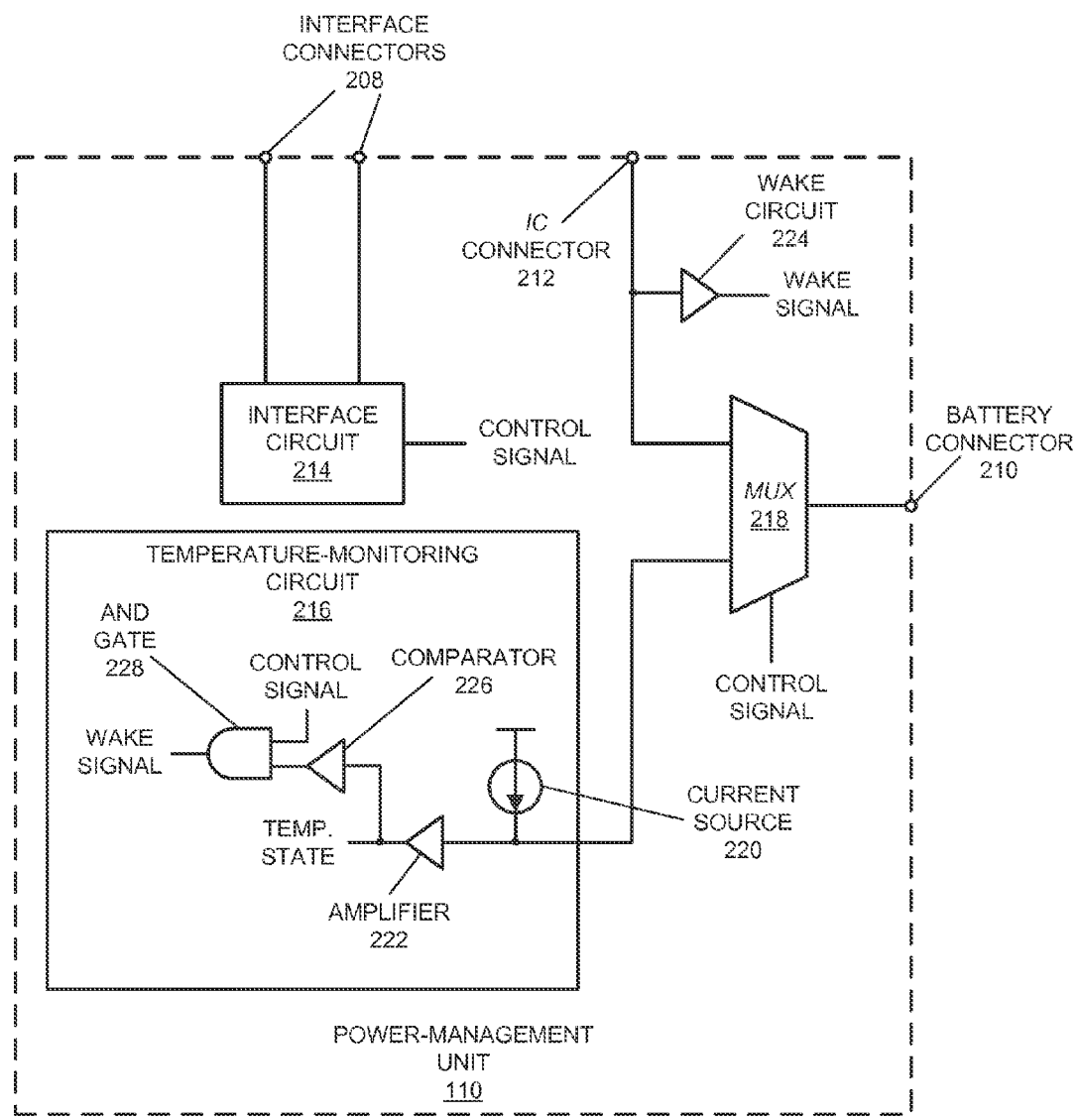
FIG. 2 presents a block diagram illustrating a power-management unit in the electronic device of FIG. 1 in accordance with an embodiment of the present disclosure.

FIG. 2 presents a block diagram illustrating power-management unit 110 (FIG. 1). Power-management unit 110 includes: battery connector 210 electrically coupled to signal line 124 (FIG. 1); an integrated-circuit (IC) connector 212 electrically coupled to integrated circuit 112 via signal line 128 (FIG. 1); an interface circuit 214 that receives a control signal (such as a timing signal) from integrated circuit 112 in FIG. 1 via interface connectors 208 (and, more generally, one or more instructions, commands or signals that are used to control multiplexer 218); a temperature-monitoring circuit 216 (or a temperature-monitoring mechanism) that monitors a temperature state of battery pack 114 and/or battery 116 in FIG. 1; and multiplexer 218. For example, the control signal may be received via an I2C bus or interface (from NXP Semiconductors, Inc. of Eindhoven, The Netherlands). However, a wide variety of communication techniques and protocols can be used to convey the control signal from integrated circuit 112 (FIG. 1) to power-management unit 110, such as a Serial Peripheral Interface Bus. Furthermore, as illustrated in FIG. 2, temperature-monitoring circuit 216 may include a current source 220 that drives a current through temperature sensor 122 (FIG. 1) and a buffer or an amplifier 222 (such as an operational amplifier) that outputs the resulting voltage that was on signal line 124 (FIG. 1).

Based on the control signal, multiplexer 218 selectively couples one of: battery connector 210 and integrated-circuit connector 212, and battery connector 210 and temperature-monitoring circuit 216. In this way, at a given time, signal line 124 (FIG. 1) conveys one of: a signal representing the temperature state, and the communication between integrated circuit 112 (FIG. 1) and battery-monitoring mechanism 120 (FIG. 1). Thus, power-management unit 110 may facilitate a reduction in the number of connectors and signal lines used to interface with battery pack 114 (FIG. 1).

Note that the temperature state may indicate whether it is safe to charge battery 116 in battery pack 114 (FIG. 1). Therefore, the temperature state may include an absolute or relative temperature of battery pack 114 and/or battery 116 (FIG. 1), which may be represented by the voltage output by amplifier 222. For example, in embodiments where temperature sensor 122 (FIG. 1) includes a thermistor, the resistance may vary between approximately 2 and 50 kΩ depending on the temperature of battery pack 114 and/or battery 116 (FIG. 1). In these embodiments, the voltage output by amplifier 222 may vary between 0.1 and 2.5 V. (Thus, the temperature state may be determined based on an analog signal provided by temperature sensor 122 in FIG. 1.) However, in other embodiments temperature-monitoring circuit 216 includes digital logic that converts the signal on signal line 124 (FIG. 1) into a digital value(s) that represents the temperature state. In these embodiments, the temperature state may include: a thermal condition of battery pack 114 and/or battery 116 (FIG. 1), such as 'safe to charge' or 'unsafe to charge'; and/or a constraint on the charging of battery pack 114 and/or battery 116 (FIG. 1) based on the temperature state (such as a charging current that may not exceed 800, 900 or 1000 mA).

Referring back to FIG. 1, as a consequence of these safety considerations, power-management unit 110 may selectively couple battery pack 114 and temperature-monitoring circuit 216 (FIG. 2) when battery pack 114 is coupled to a charger 130 (which receives power from an adapter 132 that can convert household alternating current (AC) electricity into direct current (DC) electricity for use by electronic device 100). (In FIG. 1, a return path to charger 130 may be provided via GND in electronic device 100.) As described further below with reference to FIG. 5, for safety reasons the selective coupling to the temperature-monitoring circuit 216 (FIG. 2) may be periodic (in this way, even in the event of a hardware or software failure in integrated circuit 112, the temperature state of battery pack 114 and/or battery 116 can continue to be monitored for a potentially unsafe condition). In addition, the coupling of battery pack 114 and temperature-monitoring circuit 216 (FIG. 2) may be a default configuration or condition of multiplexer 218 (FIG. 2), and power-management unit 110 may revert to this default condition a time interval (such as 500 ms) after multiplexer 218 (FIG. 2) selectively couples battery pack 114 and integrated circuit 112. In this way, the temperature state of battery pack 114 and/or battery 116 can be monitored even if the control signal is not provided by integrated circuit 112.

Note that signal line 128 coupling integrated circuit 112 and power-management unit 110 may be electrically coupled to a supply voltage (such as 1.8 V) via a pull-up resistor so that signal line 124 is pulled to the supply voltage when multiplexer 218 (FIG. 2) selectively couples integrated circuit 112 and battery pack 114.

In some embodiments where a host (e.g., integrated circuit 112) is in a power-saving mode (such as a 'sleep' mode), signal line 124 can be used to convey a wake signal from battery-monitoring mechanism 120 to transition the host to a normal operating mode (i.e., in embodiments where battery-monitoring mechanism 120 is temporarily a 'master' and integrated circuit 112 is temporarily a 'slave,' signal line 124 may be used to indicate that a condition has occurred, such as a low battery voltage, where battery-monitoring mechanism 120 wants to wake integrated circuit 112 and make it the master). Because this wake signal can be conveyed when either integrated circuit 112 or temperature-monitoring circuit 216 (FIG. 2) is selectively coupled to battery pack 114, the wake signal may be detected by a wake circuit in power-management unit 110 and/or by temperature-monitoring circuit 216 (FIG. 2).

This is shown in FIG. 2. In particular, power-management unit 110 may include a wake circuit 224 that detects the wake signal when multiplexer 218 selectively couples integrated circuit 112 (FIG. 1) to battery pack 114 (FIG. 1). For example, the wake signal may be a high-to-low conversion on signal line 124 (FIG. 1) while this signal line or bus idles at nominally 1.8 V. Moreover, as shown in FIG. 2, wake circuit 224 may include a buffer or a logic gate that can detect a digital value representing the wake signal. (Therefore, wake circuit 224 may function as a General Purpose Input/Output pin.) This digital value may be subsequently conveyed to integrated circuit 112 (FIG. 1).

Furthermore, temperature-monitoring circuit 216 may include a comparator 226 and an AND gate 228 (and, more generally, control logic) to detect the wake signal when the temperature state of battery pack 114 and/or battery 116 (FIG. 1) is being monitored. (Thus, comparator 226 and AND gate 228 may constitute a wake circuit.) In particular, when the temperature state is being monitored, the wake signal from battery-monitoring mechanism 120 may include pulling the voltage on signal line 124 (FIG. 1) below a minimum voltage level associated with temperature sensor 122 in FIG. 1 (such as a voltage below 0.1 V). This low-voltage wake signal may be detected by comparator 226. If multiplexer 218 is currently selectively coupling temperature-monitoring circuit 216 and battery pack 114 (FIG. 1), as indicated by the control signal, AND gate 228 may output a digital value indicating that the wake signal is present. This digital value may be conveyed to integrated circuit 112 (FIG. 1).

Figure 3:
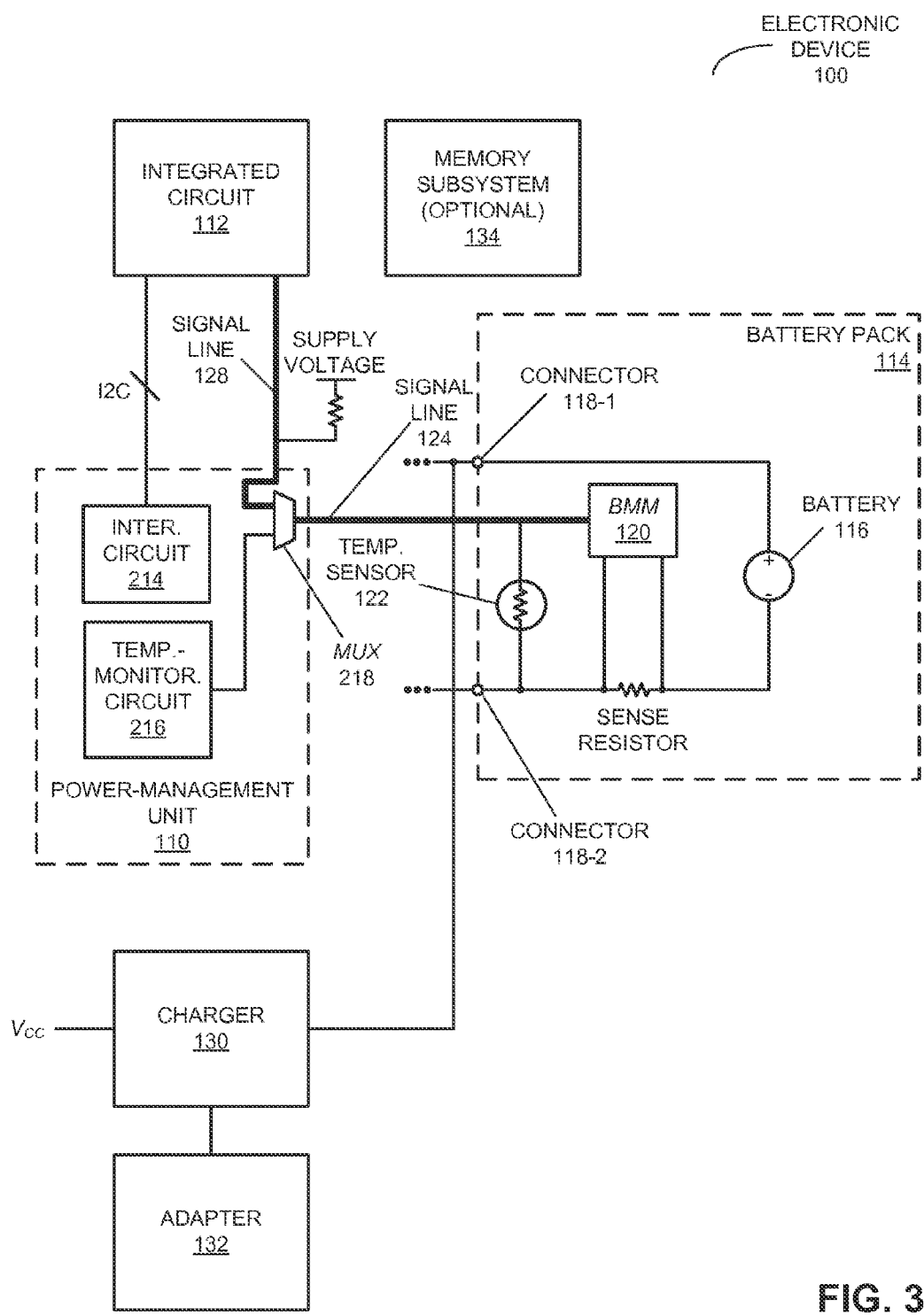
FIG. 3 presents a block diagram illustrating operation of the power-management unit of FIG. 2 in accordance with an embodiment of the present disclosure.
Figure 4:
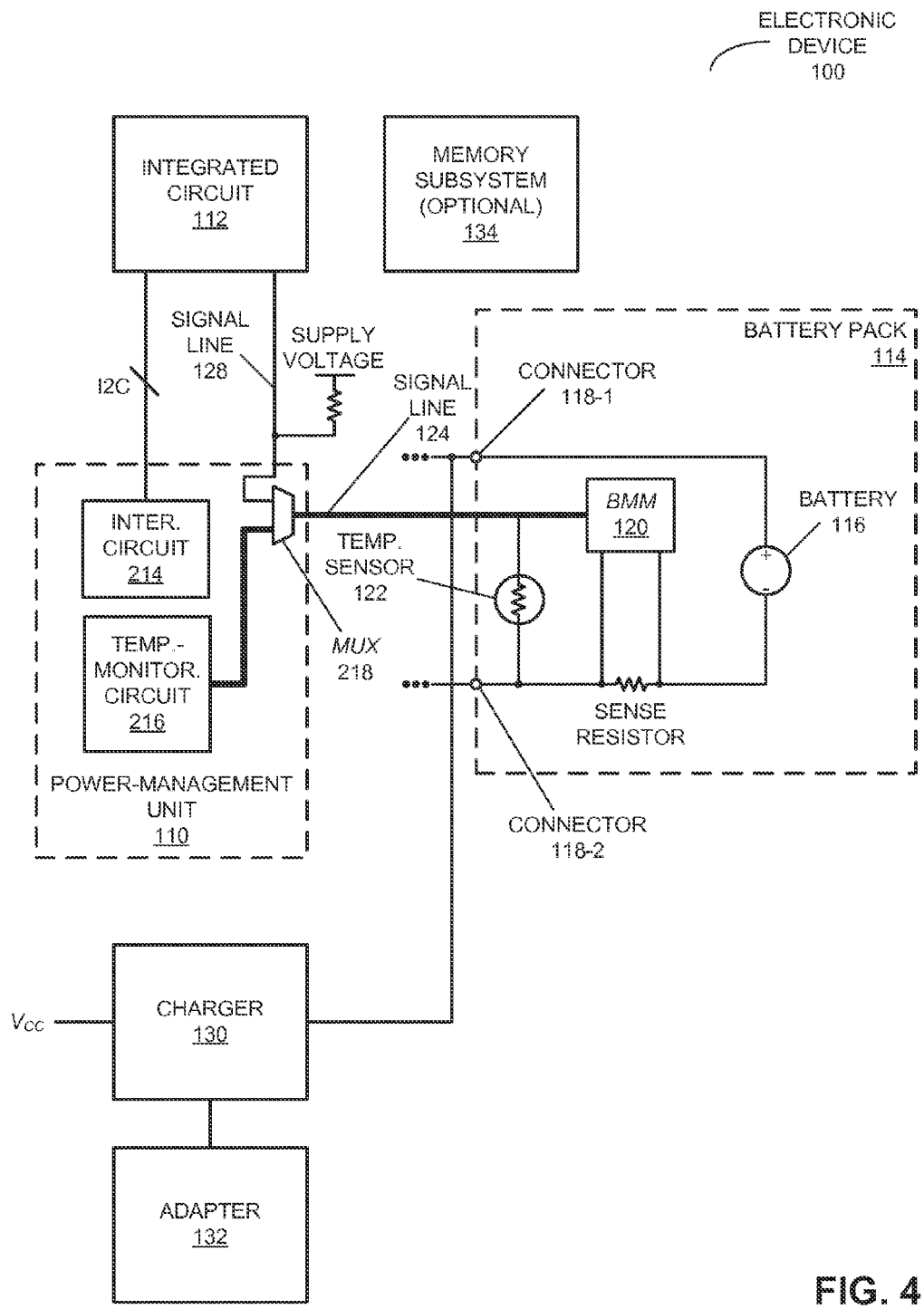
FIG. 4 presents a block diagram illustrating operation of the power-management unit of FIG. 2 in accordance with an embodiment of the present disclosure.

Operation of power-management unit 110 is further illustrated in FIGS. 3 and 4. FIG. 3 presents a block diagram illustrating operation of power-management unit 110 during a so-called 'gas-gauge mode,' in which multiplexer 218 selectively couples signal line 128 to signal line 124 (i.e., integrated circuit 112 communicates data with battery-monitoring mechanism 120), as shown by the bold line in FIG. 3. When signal line 128 is selectively coupled to signal line 124, a nominal voltage on signal line 124 may be pulled up to a supply voltage (such as 1.8 V).

As noted previously, during a subsequent 'temperature-monitoring mode,' multiplexer 218 may selectively couple temperature-monitoring circuit 216 and signal line 124 based on the control signal. Alternatively, multiplexer 218 may revert to a default condition (and, thus, the temperature-monitoring mode) a time interval after selectively coupling signal line 128 to signal line 124. As described further below with reference to FIG. 5, because of either of these mechanisms, a time duration of the gas-gauge mode may be 500 ms. More generally, the time duration may be a fraction of a thermal time constant of battery pack 114 and/or battery 116, so that the temperature state does not change appreciably during the time duration.

FIG. 4 presents a block diagram illustrating operation of power-management unit 110 during the temperature-monitoring mode. As noted previously, temperature-monitoring circuit 216 may periodically monitor the temperature state of battery pack 114 and/or battery 116, as shown by the bold line in FIG. 4. For example, as described further below with reference to FIG. 5, during the temperature-monitoring mode, temperature-monitoring circuit 216 may monitor the temperature state for 200 µs every 10 ms. Once again, this duty cycle and monitoring period may be selected based on a thermal time constant of battery pack 114 and/or battery 116, so that the temperature state does not change appreciably between determinations of the temperature state by temperature-monitoring circuit 216.

Note that transitioning from the temperature-monitoring mode to the gas-gauge mode may be initiated by integrated circuit 112 via interface circuit 214. If the host is in a power-saving or sleep mode, battery-monitoring mechanism 120 may first wake up the host by conveying the wake signal via signal line 124. After integrated circuit 112 is in the normal operating mode, it may instruct power-management unit 110 (and, thus, multiplexer 218) to transition to the gas-gauge mode.

Figure 5:
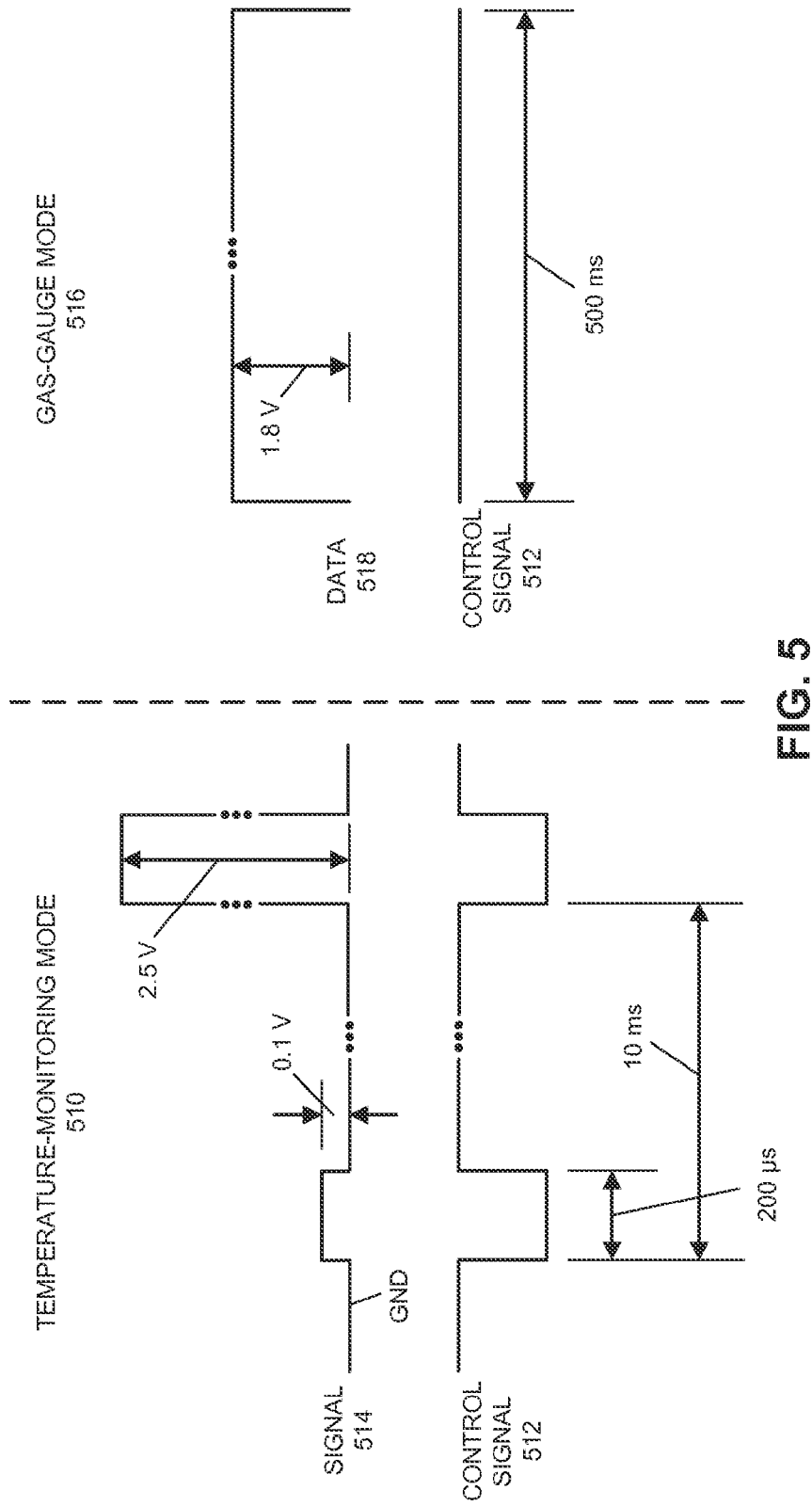
FIG. 5 presents a timing diagram illustrating operation of the power-management unit of FIG. 2 in accordance with an embodiment of the present disclosure.

FIG. 5 presents a timing diagram 500 illustrating operation of power-management unit 110. During temperature-monitoring mode 510, control signal 512 may facilitate selective coupling by multiplexer 218 of temperature-monitoring circuit 216 and temperature sensor 122 (FIGS. 1-4) for 200 µs every 10 ms. During the temperature monitoring, signal 514 on signal line 124 (FIGS. 1 and 3-4) may vary between approximately 0.1 and 2.5 V (depending on the temperature of battery pack 114 and/or battery 116 in FIGS. 1 and 3-4). Similarly, during gas-gauge mode 516, control signal 512 may facilitate selective coupling by multiplexer 218 of integrated circuit 112 and battery-monitoring mechanism 120 (FIGS. 1 and 3-4) for approximately 500 ms, so that data 518 can be transferred using a single-wire communication protocol.

Figure 6:
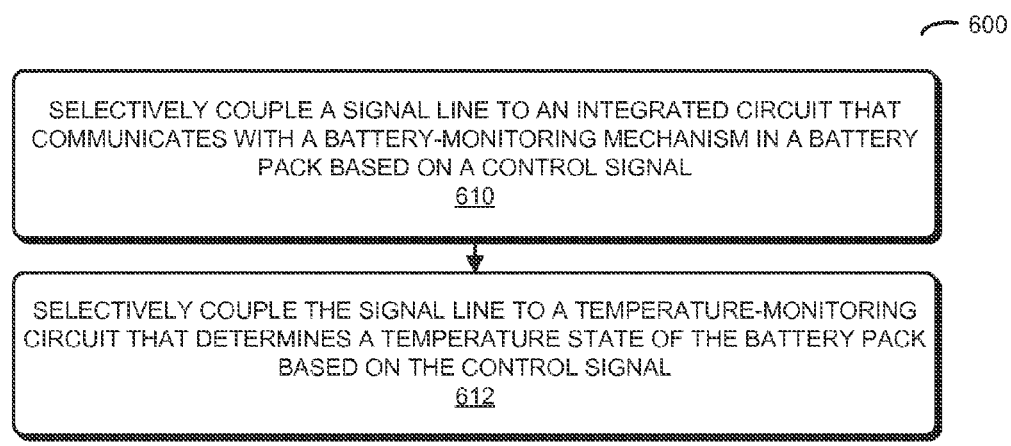
FIG. 6 presents a flowchart illustrating a method for conveying a signal that represents a temperature state of a battery pack and communicating data between an integrated circuit and the battery pack on a signal line in accordance with an embodiment of the present disclosure.

We now describe embodiments of a method. FIG. 6 presents a flowchart illustrating a method 600 for conveying a signal that represents a temperature state of a battery pack (or a battery) and communicating data between an integrated circuit and the battery pack on a signal line, which may be performed by a power-management unit (such as power-management unit 110 in FIG. 1). Based on a control signal, the power-management unit selectively couples the signal line to the integrated circuit that communicates with a battery-monitoring mechanism in the battery pack (operation 610). Subsequently, based on the control signal, the power-management unit selectively couples the signal line to a temperature-monitoring circuit that determines the temperature state of the battery pack (operation 612).

In some embodiments of method 600, there may be additional or fewer operations. Moreover, the order of the operations may be changed, and/or two or more operations may be combined into a single operation.

Referring back to FIG. 1, in general functions of the power management unit 110 may be implemented in hardware to ensure safe and reliable operation even in the face of software and/or component failures. However, in some embodiments at least some of the operations performed in electronic device 100 are implemented in software. Thus, electronic device 100 may include one or more program modules or sets of instructions stored in an optional memory subsystem 134 (such as DRAM or another type of volatile or non-volatile computer-readable memory), which may be executed by a processing subsystem in integrated circuit 112. (In general, the power-management technique may be implemented more in hardware and less in software, or less in hardware and more in software, as is known in the art.) Note that the one or more computer programs may constitute a computer-program mechanism. Furthermore, instructions in the various modules in optional memory subsystem 134 may be implemented in: a high-level procedural language, an object-oriented programming language, and/or in an assembly or machine language. Note that the programming language may be compiled or interpreted, e.g., configurable or configured, to be executed by the processing subsystem.

Components in electronic device 100 may be coupled by signal lines, links or buses. While electrical communication has been used as an illustrative example, in general these connections may include electrical, optical, or electro-optical communication of signals and/or data. Furthermore, in the preceding embodiments, some components are shown directly connected to one another, while others are shown connected via intermediate components. In each instance the method of interconnection, or 'coupling,' establishes some desired communication between two or more circuit nodes, or terminals. Such coupling may often be accomplished using a number of circuit configurations, as will be understood by those of skill in the art; for example, AC coupling and/or DC coupling may be used.

In some embodiments, functionality in these circuits, components and devices may be implemented in one or more: application-specific integrated circuits (ASICs), field-programmable gate arrays (FPGAs), and/or digital signal processors (DSPs). Furthermore, the circuits and components may be implemented using bipolar, PMOS and/or NMOS gates or transistors, and signals in these embodiments may include digital signals that have approximately discrete values and/or analog signals that have continuous values. Additionally, components and circuits may be single-ended or differential, and power supplies may be unipolar or bipolar.

Furthermore, charger 130 may include any combination of hardware and/or software implemented using analog and/or digital circuitry, and may include one or more processors, and volatile and nonvolatile memory. In some embodiments, charger 130 includes more than one chip or chip set, and in other embodiments charger 130 may operate in conjunction with a system management controller (SMC) in integrated circuit 112 that performs some of the functions of charger 130. In these embodiments, the charger and SMC may operate in a master-slave or slave-master configuration.

Additionally, battery pack 114 can be any type of battery pack capable of powering electronic device 100, and can be implemented in any technology. In some embodiments, battery pack 114 includes more than one separate battery and/or battery cell.

An output of a process for designing an integrated circuit, or a portion of an integrated circuit, comprising one or more of the circuits described herein may be a computer-readable medium such as, for example, a magnetic tape or an optical or magnetic disk. The computer-readable medium may be encoded with data structures or other information describing circuitry that may be physically instantiated as an integrated circuit or portion of an integrated circuit. Although various formats may be used for such encoding, these data structures are commonly written in: Caltech Intermediate Format (CIF), Calma GDS II Stream Format (GDSII) or Electronic Design Interchange Format (EDIF). Those of skill in the art of integrated circuit design can develop such data structures from schematics of the type detailed above and the corresponding descriptions and encode the data structures on a computer-readable medium. Those of skill in the art of integrated circuit fabrication can use such encoded data to fabricate integrated circuits comprising one or more of the circuits described herein.

Electronic device 100 may include a variety of devices that can include a battery pack, and that can receive electrical current from an adapter and a charger, including: a laptop computer, a media player (such as an MP3 player), an appliance, a subnotebook/netbook, a tablet computer, a smartphone, a cellular telephone, a network appliance, a set-top box, a personal digital assistant (PDA), a toy, a controller, a digital signal processor, a game console, a device controller, a computational engine within an appliance, a consumer-electronic device, a portable computing device or a portable electronic device, a personal organizer, and/or another electronic device.

Although we use specific components to describe electronic device 100, in alternative embodiments, different components and/or subsystems may be present in electronic device 100. For example, battery 114 may include a protective circuit to prevent battery 116 from being damaged during operation. Additionally, one or more of the components may not be present in electronic device 100. Moreover, in some embodiments, electronic device 100 may include one or more additional components that are not shown in FIG. 1. Also, although separate components are shown in FIG. 1, in some embodiments, some or all of a given component can be integrated into one or more of the other components in electronic device 100 and/or positions of components in electronic device 100 can be changed.

In the preceding description, we refer to 'some embodiments.' Note that 'some embodiments' describes a subset of all of the possible embodiments, but does not always specify the same subset of the embodiments.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. A power-management unit, comprising:
    a battery connector configured to couple to a signal line from a battery pack;
    an integrated-circuit connector configured to couple to an integrated circuit that communicates with a battery-monitoring mechanism located in the battery pack;
    an interface circuit configured to receive a control signal from the integrated circuit;
    a temperature-monitoring circuit external to the battery pack and configured to monitor a temperature state of the battery pack via the signal line; and
    a multiplexer, coupled to the battery connector, the integrated-circuit connector, the interface circuit, and the temperature-monitoring circuit, configured to selectively couple, based on the control signal, one of: the battery connector and the integrated-circuit connector, and the battery connector and the temperature-monitoring circuit, so that, at a first time, the signal line conveys a signal representing the temperature state and at a second time the signal line conveys the communication between the integrated circuit and the battery-monitoring mechanism.

2. The power-management unit of claim 1, wherein the multiplexer periodically couples the battery connector and the temperature-monitoring circuit.

3. The power-management unit of claim 1, wherein a default condition of the multiplexer couples the battery connector and the temperature-monitoring circuit; and
    wherein the power-management unit is configured to place the multiplexer in the default condition after a predetermined interval of time has elapsed since the multiplexer's selectively coupling the battery connector and the integrated-circuit connector.

4. The power-management unit of claim 1, wherein the integrated-circuit connector is further configured to couple to a supply voltage via a pull-up resistor so that the signal line is pulled to the supply voltage when the multiplexer selectively couples the battery connector and the integrated-circuit connector.

5. The power-management unit of claim 1, wherein, via the multiplexer, the power-management unit is configured to selectively couple the battery connector and the temperature-monitoring circuit when the battery pack is coupled to a charger.

6. The power-management unit of claim 1, wherein the temperature state indicates whether it is safe to charge the battery pack.

7. The power-management unit of claim 1, wherein the power-management unit further includes a wake circuit, the wake circuit coupled to the integrated-circuit connector, and coupleable to the battery-monitoring mechanism via the signal line,
    wherein the wake circuit is configured to detect a wake signal from the battery-monitoring mechanism on the signal line and upon such detection, cause the integrated circuit to transition from a power-saving mode to a normal operating mode.

8. The power-management unit of claim 1, wherein the temperature-monitoring circuit is configured to detect a wake signal on the signal line when monitoring the temperature state of the battery pack, and upon such detection, cause the integrated circuit to transition from a power-saving mode to a normal operating mode.

9. A method for conveying a signal representing a temperature state of a battery pack and communicating data between an integrated circuit and the battery pack on a signal line, the method comprising:
    receiving a control signal from the integrated circuit;
    selectively coupling, based on the control signal, the signal line to the integrated circuit that communicates with a battery-monitoring mechanism inside the battery pack; and
    selectively coupling, based on the control signal, the signal line to a temperature-monitoring circuit external to the battery pack that determines a temperature state of the battery pack;
    such that at a first time, the signal line conveys a signal representing the temperature state and at a second time the signal line conveys the communication between the integrated circuit and the battery-monitoring mechanism.

10. An electronic device, comprising:
    a battery pack, wherein the battery pack includes:
        a battery;
        a battery-monitoring mechanism, coupled to the battery, located in the battery pack and configured to monitor characteristics of the battery;
        a temperature sensor; and
        a signal line coupled to the battery-monitoring mechanism and the temperature sensor;
    an integrated circuit configured to provide a control signal and to communicate with the battery-monitoring mechanism; and
    a power-management unit, wherein the power-management unit includes:
        an interface circuit, coupled to the integrated circuit, configured to receive the control signal;
        a temperature-monitoring circuit configured to monitor a temperature state of the battery pack via the signal line; and
        a multiplexer, coupled to the signal line, the integrated circuit, the interface circuit and the temperature-monitoring circuit, configured to selectively couple, based on the control signal, one of: the signal line and the integrated circuit, and the signal line and the temperature-monitoring circuit, so that, at a first time, the signal line conveys a signal representing the temperature state and at a second time the signal line conveys a signal representing the communication between the integrated circuit and the battery-monitoring mechanism.

11. The electronic device of claim 10, wherein the multiplexer periodically couples the battery pack and the temperature-monitoring circuit.

12. The electronic device of claim 10,
    wherein a default condition of the multiplexer couples the battery pack and the temperature-monitoring circuit; and
    wherein the power-management unit is configured to place the multiplexer in the default condition after a predetermined amount of time has passed since the multiplexer selectively coupled the battery pack and the integrated circuit.

13. The electronic device of claim 10, wherein, via the multiplexer, the power-management unit is configured to selectively couple the battery pack and the temperature-monitoring circuit when the battery pack is coupled to a charger.

14. The electronic device of claim 10, wherein the temperature state indicates whether it is safe to charge the battery pack.

15. The electronic device of claim 10, wherein the power-management unit further includes a wake circuit, the wake circuit coupled to the integrated-circuit connector, and coupleable to the battery-monitoring mechanism via the signal line,
   wherein the wake circuit is configured to detect a wake signal from the battery-monitoring mechanism on the signal line and upon such detection, cause the integrated circuit to transition from a power-saving mode to a normal operating mode.

16. The electronic device of claim 10, wherein the temperature-monitoring circuit is configured to detect a wake signal on the signal line when monitoring the temperature state and upon such detection transition the integrated circuit from a power-saving mode to a normal operating mode.

17. The power-management unit of claim 1 wherein the signal representing the temperature state is an analog signal and wherein the communication between the integrated circuit and the battery-monitoring mechanism is digital communication.

18. The method of claim 9 wherein the signal representing a temperature state of the battery pack is an analog signal and the data communicated between the integrated circuit and the battery pack is digital data.

19. The electronic device of claim 10 wherein the signal representing the temperature state is an analog signal and the signal representing the communication between the integrated circuit and the battery-monitoring mechanism is a digital signal.

* * * * *